United States Patent
Madsen et al.

(10) Patent No.: US 12,396,678 B2
(45) Date of Patent: Aug. 26, 2025

(54) POSTURAL AWARENESS AND EXERCISE DEVICE

(71) Applicant: M&H INNOVATIONS LLC, Santa Barbara, CA (US)

(72) Inventors: Marianne Madsen, Santa Barbara, CA (US); Holli Michaels, Santa Barbara, CA (US)

(73) Assignee: M&H INNOVATIONS LLC, Santa Barbara, CA (US)

( * ) Notice: Subject to any disclaimer, the term of this patent is extended or adjusted under 35 U.S.C. 154(b) by 0 days.

(21) Appl. No.: 19/037,278

(22) Filed: Jan. 26, 2025

(65) Prior Publication Data
US 2025/0169745 A1    May 29, 2025

Related U.S. Application Data

(63) Continuation of application No. PCT/US2024/033685, filed on Jun. 12, 2024.

(60) Provisional application No. 63/508,472, filed on Jun. 15, 2023.

(51) Int. Cl.
*A61B 5/00*    (2006.01)

(52) U.S. Cl.
CPC ........ *A61B 5/4561* (2013.01); *A61B 2505/09* (2013.01); *A61B 2560/0462* (2013.01)

(58) Field of Classification Search
CPC . A61B 5/4561; A61B 5/1116; A61B 2505/09; A61B 2560/0462; A63B 23/0244
See application file for complete search history.

(56) References Cited

U.S. PATENT DOCUMENTS

| | | | |
|---|---|---|---|
| 6,487,906 B1 * | 12/2002 | Hock ................... | A61B 5/1126 73/379.01 |
| 10,383,548 B2 * | 8/2019 | Brandon .......... | A63B 21/00196 |
| 2002/0151824 A1 | 10/2002 | Fischer | |
| 2012/0245491 A1 | 9/2012 | Amell et al. | |
| 2012/0259573 A1 | 10/2012 | Mehnert et al. | |
| 2019/0175093 A1 | 6/2019 | Suzuki | |
| 2020/0288999 A1 | 9/2020 | Lasarov et al. | |

FOREIGN PATENT DOCUMENTS

KR    102089848 B1    3/2020

OTHER PUBLICATIONS

Oct. 10, 2024, USPTO, International Search Report and Written Opinion for PCT/US2024/033685.

\* cited by examiner

*Primary Examiner* — Devin B Henson
(74) *Attorney, Agent, or Firm* — Invention To Patent Services; Alex Hobson

(57) ABSTRACT

A postural awareness device provides feedback when the lumbar is press down against a lumbar sensor to move a magnet toward a hall effect sensor or sensors. The magnet is configured in a sensor body that extends from a posture training mat and is resilient, wherein the sensor body can be compressed by the lumbar and then spring back to an original shape. A feedback device may include a light device, a vibration device and/or a sound device. The feedback signal, light, vibration or sound may initiate when the magnet is actuated by compression of the sensor body toward the posture training mat. The feedback signal may then change intensity or frequency as the magnet is actuated further toward the hall effect sensor. A feedback light may change color as the magnet is brought closer to the hall effect sensor.

14 Claims, 6 Drawing Sheets

POSTURAL AWARENESS AND EXERCISE DEVICE

CROSS REFERENCE TO RELATED APPLICATIONS

This application is a continuation of international patent application No. PCT/US24/33685, having an international filing date of Jun. 12, 2024, which claims the benefit of priority to U.S. provisional patent application No. 63/508,472, filed on Jun. 15, 2023; the entirety of both applications are hereby incorporated by reference herein.

BACKGROUND OF THE INVENTION

Field of the Invention

The invention relates a postural awareness and exercise device that provides feedback when the lumbar is press down against a lumbar sensor in a pelvic tilt to move a magnet more proximal to a hall effect sensor.

Background

Maintaining a good posture is important to prevent back pain and injury. To maintain good posture, core muscles and muscles along the back are required. Strengthening muscles to maintain good posture makes it easier for people to maintain posture throughout the day. An exercise that is helpful to strengthen these muscles is a pelvic tilt, wherein a person lays on their back and presses their lumbar, or lower back down toward the ground. The person may then hold this position for a period of time to engage and strengthen core and back or lumbar muscles. It is important to compress or press the lumbar uniformly down to prevent injury. Proper alignment is an important consideration while performing these exercises.

SUMMARY OF THE INVENTION

The invention is directed to a postural awareness device that provides feedback when the lumbar is press down against a lumbar sensor to move a magnet more proximal to a hall effect sensor or sensors. The magnet is configured in a sensor body that extends from a posture training mat and is resilient, wherein the sensor body can be compressed by the lumbar and then spring back to an original shape. A feedback device may include a light device, a vibration device and/or a sound device. The feedback signal, light, vibration or sound may initiate when the magnet is actuated by compression of the sensor body toward the posture training mat. The feedback signal may then change intensity or frequency as the magnet is actuated further toward the hall effect sensor. A light device may change color as the magnet is brought closer to the hall effect sensor. Also, the feedback devices may produce alerting feedback if the pelvic tilt is not being performed in alignment along a centerline of the posture training mat. This alerting feedback may prevent injury from out of alignment pelvic tilts. Also, the feedback devices may provide encouraging feedback to the user to compress the sensor body further or exercise more often, thereby improving their ability to maintain posture.

The posture training mat extends a length from a head end to a feet end along a length axis and has a width from opposing left and right sides. The length of the posture training mat may be about 0.5 m or more, about 0.75 m or more, about 1 m or more, or from about 0.5 m to 1 m or any other range between and including the values provided. The width may be about 0.25 m or more, about 0.35 m or more, about 0.5 m or more, about 0.6 m or more, about 0.75 m or more, or from about 0.25 to about 0.75 m. The width may vary along the length axis and the width proximal to the head end may be greater than the width in the middle or proximal to the feet end. The posture training mat 80 may have an hour-glass shape wherein the width tapers in along a middle portion between the head end and feet end. A sloped surface of the posture training mat may extend down toward the feet end for more comfort when lying on the posture training mat. The posture training mat has a centerline axis extending centrally across the width of the posture training mat from the feet end to the head end, aligned with the length axis. The posture training mat has an edge around the perimeter between the interface surface 94 and base surface 96.

The postural awareness device may have alignment features that extend from the interface surface of the posture training mat. The alignment features may be small handles or protrusions from the posture training mat that enable a person to center themselves on the mat along the length axis, or centerline axis. Also, the posture training mat may have a friction material along the base surface to prevent the posture training mat from slipping during use. A friction material may have a coefficient of friction of about 0.5 or more, about 0.6 or more or even 0.7 or more, according to ASTM C1028. The friction material 89 may include an elastomeric material such as urethane or silicone which provides a high friction on most flooring surfaces. The coefficient of friction (COF) value is expressed as a number between 0.0 and 1.0. The closer the number is to 1.0 the greater the slip resistance provided. Surfaces with high coefficients of friction (COF 0.6 or higher) are generally rough and hence provide grip for the person during movement. The United States ANSI method (ASTM C1028) gives, through the use of a force gauge (horizontal dynamometer) pull meter method, the static friction coefficient of the surface.

A postural awareness device includes the posture training mat with a lumbar sensor coupled thereto. The lumbar sensor has a pliable sensor body that upon compressing an effective amount provides feedback via light devices and/or a vibration via a vibration device and/or a sound via a sound device. A magnet is configured in sensor body, such as along a pliable extension of the sensor body, and may be attached to the inside surface of the pliable extension or molded within the pliable extension. A sensor body may have one or more sensor body apertures to further aid in compression of the sensor body. A sensor body aperture may be configured through opposing sides of the pliable extension. A sensor body may have a void within an interior or between the pliable extension and the posture training mat. An elastomeric material may be configured within the pliable extension, such as an elastomeric foam.

One or more hall effect sensors are configured with the posture training mat and when the magnet is actuated toward the hall effect sensors, the hall effect sensors can detect the sensor distance, a distance of the magnet from the hall effect sensor. The sensor distance indicates an amount of compression of the sensor body. The feedback device or devices may initiate when the sensor distance falls below a first threshold distance and may change intensity, and/or frequency as the sensor distance further reduces. The magnet may be configured a sensor distance from the hall effect sensors, such as about 25 mm or more, about 35 mm or more, about 50 mm or more, about 65 mm or more, about 75 mm or more, about 85 mm or more, about 100 mm or more and any range between and including the values provided. A magnet may have to be actuated down toward the hall effect sensors to initiate a feedback device and the magnet may have to be move with a threshold sensor distance from the hall effect sensors, such as about 100 mm or less, about 75 mm or less, about 65 mm or less, about 50 mm or less, about 35 mm or less, about 25 mm or less and any range between and including the values provided.

Light devices may be coupled to the posture training mat and illuminate to produce a feedback light when the sensor body is compressed an effective amount to move the magnet toward the hall effect sensors. The light devices may be configured along a perimeter of the posture training mat. The light device may include a plurality of individual light devices, such as light emitting diodes, and may include two or more, three or more, five or more, ten or more, 20 or more, 40 or more, 60 or more, and any range between and including the numbers provided. The light device may produce a feedback light that change in color as the sensor body is compress during a pelvic tilt. Also, an alerting signal of a light device may be an alerting color, such as yellow or red light. A light device may indicate an improper position of the magnet or that the magnet has not been actuated uniformly toward the hall effect sensors during a pelvic tilt, wherein the magnet distance from a first hall effect sensor is a threshold sensor distance differential from the distance of the magnet to a second hall effect sensor. If the sensor distance differential is above a threshold this indicates a pelvic tilt that is not in alignment along the centerline of the posture training mat, which can result in injury. The color of the feedback light may be different from a feedback light to indicate a proper pelvic tilt in alignment and above a threshold compression of the sensor body. The feedback light may flash or flash at a different frequency to indicate improper alignment.

A vibration device such as a haptic vibration device, may also be coupled with the posture training mat and vibrate when the sensor body is compressed to bring the magnet within a threshold sensor distance from the hall effect sensor such as to a threshold sensor distance from the hall effect sensors. A feedback vibration produced by the vibration device may indicate proper pelvic tilt that is above a threshold compression and in alignment with the centerline of the posture training mat. Also, a feedback vibration may indicate that the magnet has not been actuated uniformly toward the hall effect sensors during a pelvic tilt, wherein the magnet distance from a first hall effect sensor is a threshold sensor distance differential from the distance of the magnet to a second hall effect sensor. The amplitude and/or the frequency of the feedback vibration may be different from a feedback vibration to indicate a proper pelvic tilt in alignment and above a threshold compression of the sensor body.

A sound device is configured to make an audible sound when the sensor body is compressed to actuate the magnet toward the hall effect sensors, such as to a threshold sensor distance from the hall effect sensors. Again, the sound intensity and/or frequency may change as the magnet is actuated toward the hall effect sensor and may change intensity, tone or frequency as an alerting signal that the pelvic tilts not being performed in alignment with the centerline axis of the posture training mat.

A person may exercise their lumbar, core and back muscles, on a postural awareness device by lying on the posture training mat and pressing their lumbar down toward the interface surface of the mat to compress the sensor body. The person may utilize alignment features, protrusions from the mat to align themselves along the length axis or centerline axis of the posture training mat with their head extending from the head end of the posture training mat and their feet distal the feet end of the posture training mat. When aligned with the length axis, the person's spine will extend along the centerline axis of the posture training mat. The centerline axis extends centrally between the left and right sides of the posture training mat and along the length axis. After getting aligned, the person may then press their lower back or lumbar down to compress the sensor body, such as the pliable extension of the sensor body, and move the magnet toward the hall-effect sensors to initiate one or more of the feedback devices to activate.

An exemplary postural awareness device includes a plurality of components that are configured to enable ease of use and effective feedback of proper lumbar positioning during an exercise. The posture training mat may have a base layer, which may have a friction material configured thereon to prevent slipping or sliding of the posture training mat during use, an interface layer and may have a middle layer. Each of the layers may be a foam and may be foams of different durometer to provide the proper resistance to compression and comfort during exercise. A cover layer may be configured over the interface layer to protect the interface layer from getting contaminated with sweat. The cover layer may be water resistant or waterproof and may have an attractive design and or logos printed thereon. A lumber sensor aperture may be configured through the cover layer, the interface layer and also the middle layer to enable the lumbar sensor body to extend therethrough to the base layer. A frame component may extend around a portion of the posture training mat, such as along or around an edge of the posture training mat. The frame component may be a rigid material such as a plastic formed frame. The feedback device or devices, may be coupled to the frame component. In an exemplary embodiment, the light devices are coupled to the frame and emit light from said edge of the posture training mat. The frame component may extend around the head end of the posture training mat and down along the sides toward the feet end.

The postural awareness device may be controlled by a controller that may have a microprocessor and/or a circuit board to control the functions of the device. The hall effect sensors may provide an input to the controller when the magnet is actuated within a threshold sensor distance of the hall effect sensor and the controller may then initiate the light devices to produce feedback lights and/or the vibration devices to vibrate to produce a feedback vibration, and or the sound device to emit a feedback sound. The system may have a battery to power the electronic components and an on/off switch.

The lumbar sensor may include a plurality of hall effect sensors 62 arranged to detect compression of the sensor body in alignment with the centerline of the posture training mat. The arrangement of the hall effect sensors, such as on a hall effect board enables the controller to determine if the pelvic tilt is being performed uniformly or along the centerline axis of the posture training mat. A plurality of hall effect sensor may be configured with a length offset distance along the length axis or centerline axis and also a width offset distance orthogonal from the length axis, or across the width of the posture training mat. An exemplary lumbar sensor may include a plurality of hall effect sensors to determine proper pelvic tilt such as two or more, three or more, four or more, five or more, six or more and any range between and including the numbers provided. A plurality of hall effect sensors may be arranged in a triangular array with two hall effect sensors offset a width offset distance from the centerline axis and a third hall effect sensor configured along a length offset distance from said two hall effect sensors. The third hall effect sensor may be configured along the centerline axis.

The width offset distance of hall effect sensors across the centerline, may be about 10 mm or more, about 20 mm or more, about 30 mm or more, about 50 mm or more, and any range between and including the width offset distances provided. Likewise, hall effect sensors may be configured a length offset distance along the length of the posture training mat about 10 mm or more, about 20 mm or more, about 30 mm or more, about 50 mm or more, and any range between and including the length offset distances provided.

The light devices may illuminate different color light depending on the sensor distance achieved by the compression of the sensor body by the lumbar. A blue light may illuminate from a light device when in a resting position. A green light may illuminate from a light device when a person is in a proper position on the posture awareness mat and has actuated the magnets threshold distance toward the hall effect sensor. A red light may indicate an improper position of the magnet or that the magnet has not been actuated uniformly toward the hall effect sensors. As described herein a plurality of hall effect sensors may each detect a distance from the magnet and therefore a discrepancy in this measured distance from one hall effect sensor to another may initiate the red light to illuminate from a light device.

Likewise, the vibration device(s) may vibrate at a particular frequency and intensity or amplitude when the magnet is forced to a first threshold distance, a sensor distance within a particular range or below a threshold, and then vibrate at a different frequency and/or amplitude when the magnet is forced further down toward the hall effect sensor to a smaller threshold distance, a smaller sensor distance. The vibration frequency may change continuously as a function of the threshold distance or may have steps in frequency for different set threshold distances.

Likewise, the sound device may emit a particular sound tone, intensity or volume of sound, and/or frequency of sound, when the magnet is forced to a first threshold distance, a sensor distance within a particular range or below a threshold, and then emit a different sound, sound level or different frequency when the magnet is forced further down toward the hall effect sensor to a smaller threshold distance, a smaller sensor distance. The sound device may change the sound emitted continuously as a function of the threshold distance or may have steps in frequency for different set threshold distances. For example, the sound frequency may start of after a first threshold sensor distance is achieved and then the frequency may be increased as the sensor distance is reduced by the compression of the sensor body.

A postural awareness system may utilize a mobile electronic device, such as a mobile phone or tablet computer to interface with the postural awareness device and produce a feedback signal, and/or provide other feedback such as the number of pelvic tilt repetitions performed, the amount of compression of the sensor body as determined by the hall effect sensors, the alignment of compression as determined by the hall effect sensors. A mobile device has an interface screen that may be used to interface with the postural awareness device. The interface screen may display a feedback light or feedback symbol or text to let a user know if they are aligned and compressing the sensor body uniformly or in alignment during pelvic tilts. Also, a mobile electronic device may have a sound device that emits feedback sound, again to indicate actuation of the magnet to within a threshold sensor distance from the hall effect sensors and/or alignment of compression. Also, a mobile device may have a vibration device that produces a feedback vibration. The vibration device may be the standard vibration device of a mobile phone and the sound device may be the standard speaker of a mobile phone and the display screen may display a color or symbol from the standard display screen or interface touch screen of the mobile phone.

The summary of the invention is provided as a general introduction to some of the embodiments of the invention, and is not intended to be limiting. Additional example embodiments including variations and alternative configurations of the invention are provided herein.

BRIEF DESCRIPTION OF SEVERAL VIEWS OF THE DRAWINGS

The accompanying drawings are included to provide a further understanding of the invention and are incorporated in and constitute a part of this specification, illustrate embodiments of the invention, and together with the description serve to explain the principles of the invention.

Figure 1:
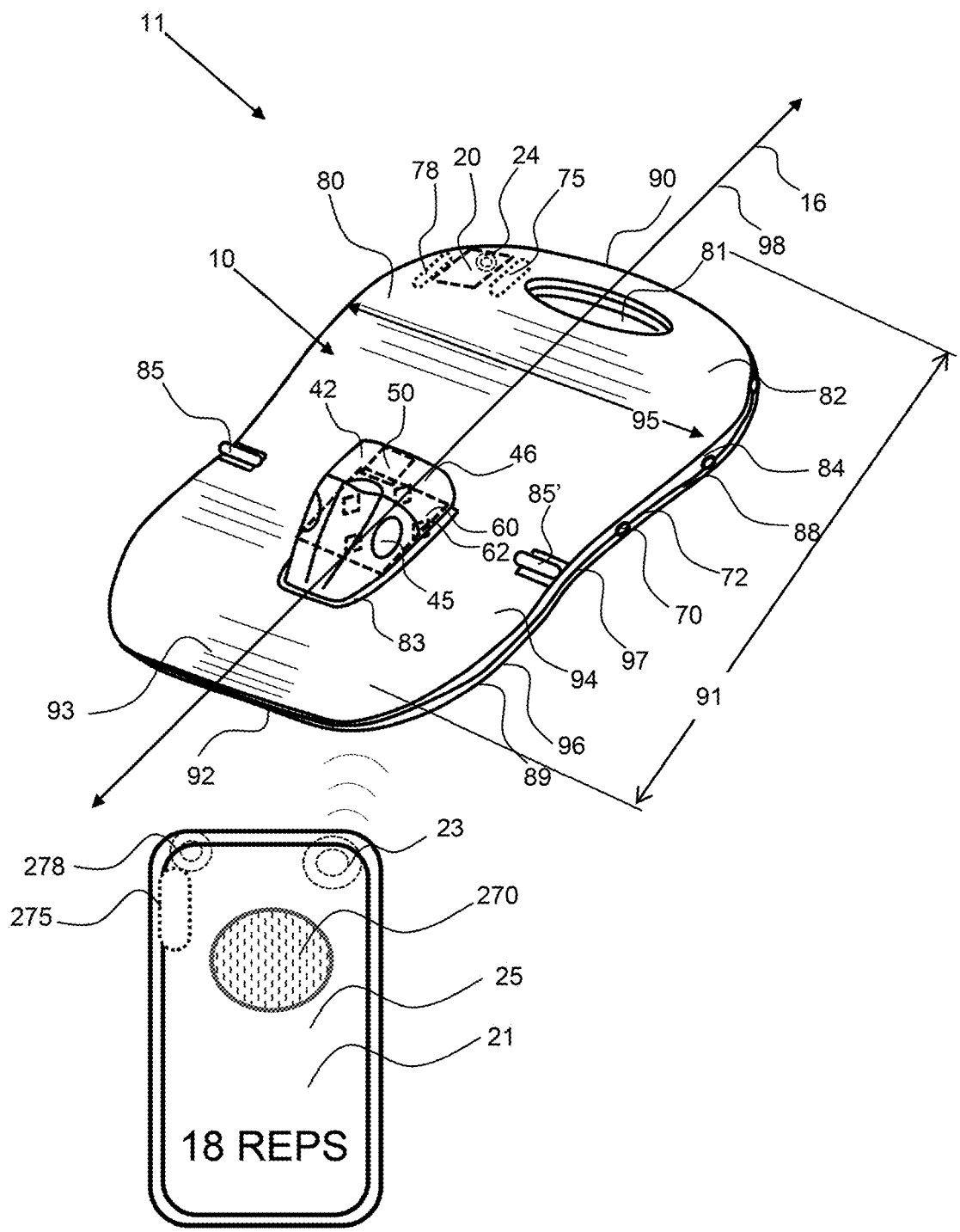
FIG. 1 shows a perspective view of postural awareness device including a lumbar sensor with a pliable sensor body that upon compression an effective amount provides feedback via light devices and/or a vibration device and/or a sound device.

Corresponding reference characters indicate corresponding parts throughout the several views of the figures. The figures represent an illustration of some of the embodiments of the present invention and are not to be construed as limiting the scope of the invention in any manner. Some of the figures may not show all of the features and components of the invention for ease of illustration, but it is to be understood that where possible, features and components from one figure may be included in the other figures. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

DETAILED DESCRIPTION OF THE ILLUSTRATED EMBODIMENTS

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Certain exemplary embodiments of the present invention are described herein and are illustrated in the accompanying figures. The embodiments described are only for purposes of illustrating the present invention and should not be interpreted as limiting the scope of the invention. Other embodiments of the invention, and certain modifications, combinations and improvements of the described embodiments, will occur to those skilled in the art and all such alternate embodiments, combinations, modifications, improvements are within the scope of the present invention.

Referring now to the Figures and with particular reference to FIG. 1, a postural awareness device 10 includes a posture training mat 80 with a lumbar sensor 40 coupled thereto. The lumbar sensor has a pliable sensor body 42 that upon compressing an effective amount provides feedback via light devices 70, and/or a vibration via a vibration device 75 and/or a sound via a sound device 78. A magnet 50 is configured in a pliable extension 46 of the sensor body 42, and may be attached to the inside surface of the pliable extension or molded within the pliable extension. A sensor body 42 may have one or more sensor body apertures 45 to further aid in compression of the sensor body. A sensor body aperture 45 may be configured through opposing sides of the pliable extension 46, as shown in FIG. 1. A plurality of hall effect sensor 62 are configured with the posture training mat 80 and when the magnet 50 approaches the hall effect sensors, the amount of compression is detected by the hall effect sensors. Light devices 70, or light devices, are coupled to the posture training mat 80 and illuminate when the sensor body is compressed an effective amount to move the magnet toward the hall effect sensors 62. As shown, the light devices 70 are configured along a perimeter of the posture training mat 80. A vibration device 75, such as a haptic vibration device, is also coupled with the posture training mat 80 and vibrates when the sensor body is compressed to bring the magnet within a proximity sensor distance to the hall effect sensor 62. A sound device is configured to make a audible sound when the sensor body is compressed to actuate the magnet toward the hall effect sensors.

The posture training mat 80 extends a length 91 from a head end 90 to a feet end 92 along a length axis 16 and has a width 95 from opposing left and right sides. As shown the width may vary along the length axis and the width proximal to the head end 90 may be greater than the width in the middle or proximal to the feet end 92. The posture training mat 80 may have a handle 81, such as an aperture through the mat proximal to the head end 90 of the mat. Also, as shown, the posture training mat 80 may have an hour-glass shape wherein the width tapers in along a middle portion between the head end and feet end. A sloped surface 93 may extend down toward the feet end 92 for more comfort when lying on the posture training mat 80. The posture training mat 80 has a centerline axis 98 extending centrally across the width of the posture training mat 80 from the feet end 92 to the head end 90, aligned with the length axis. The posture training mat 80 has an edge 97 around the perimeter between the interface surface 94 and base surface 96.

Figure 3:
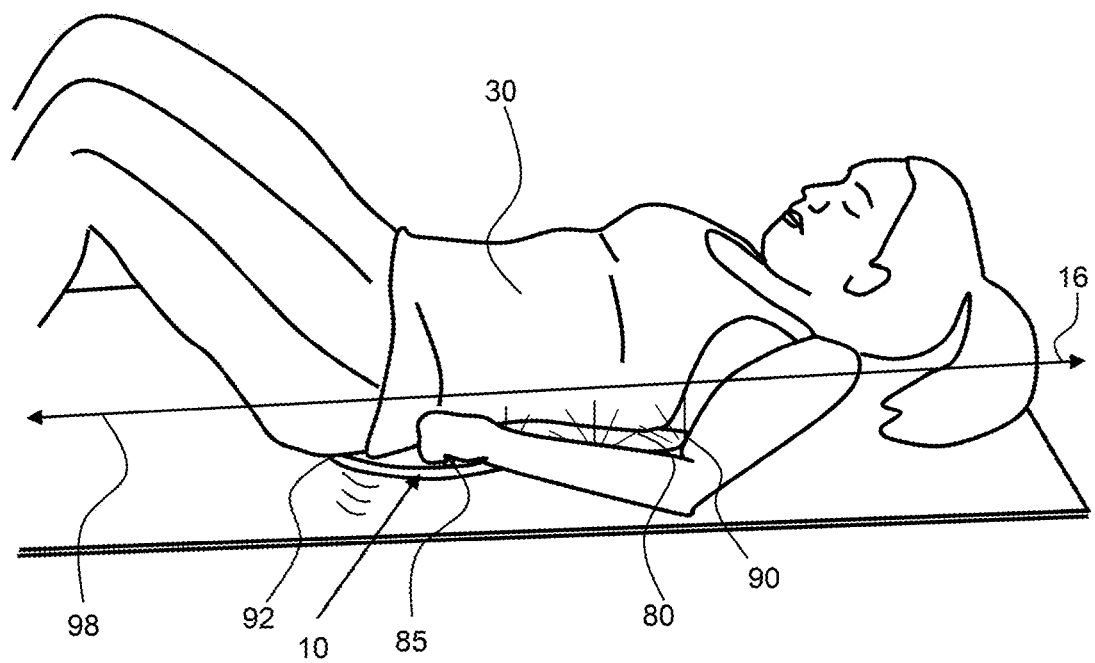
FIG. 3 shows a person exercising and pressing their lower back or lumbar down to compress the elastomeric component of the lumbar sensor and move the magnet toward the hall-effect sensor to initiate the feedback of a light and/or a vibration from a vibration sensor, and shows the person aligned on the posture training mat by holding the alignment features.
Figure 5:
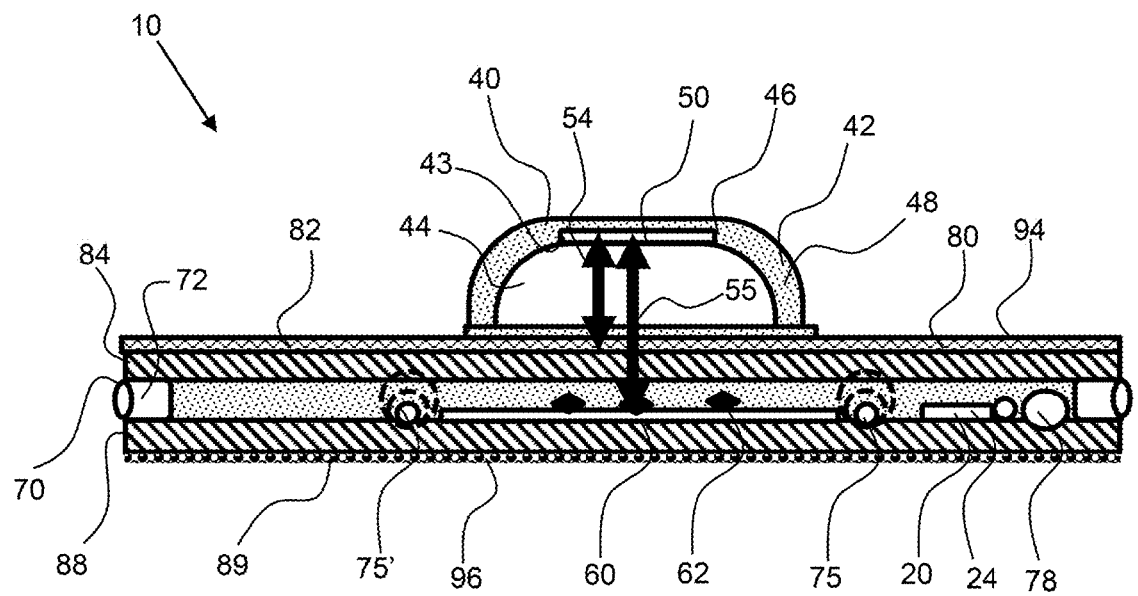
FIG. 5 shows a cross sectional view of an exemplary postural awareness device having a lumbar sensor utilizing a magnet configured in a pliable extension of the sensor body and hall effect sensors configured on a hall effect board coupled to the posture training mat.
Figure 6:
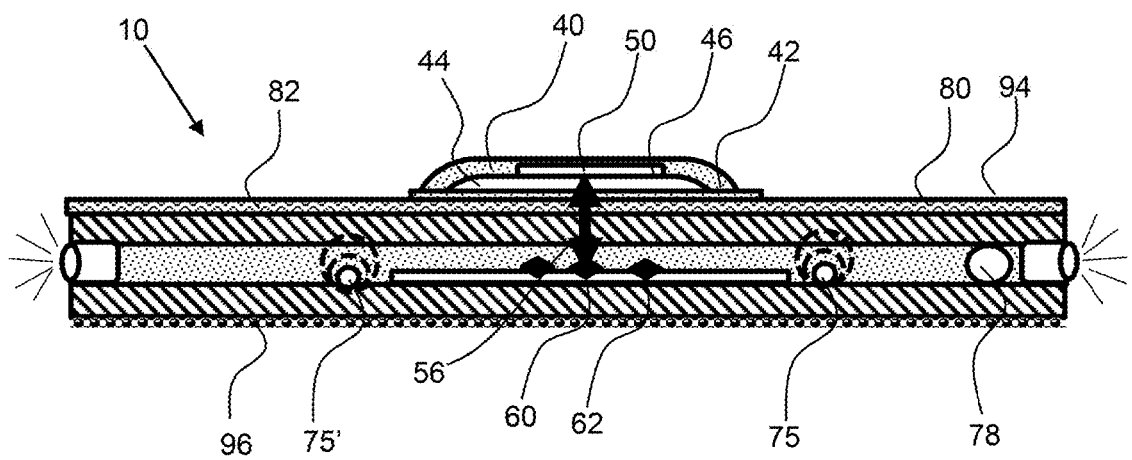
FIG. 6 shows a cross sectional view of the exemplary postural awareness device shown in FIG. 5, with the sensor body compressed to move the magnet to reduce the sensor distance and initiate feedback in the way of light and/or vibration and/or sound.

The postural awareness device 10 may have alignment features 85, 85' that extend from the interface surface 94 of the posture training mat 80. The alignment features may be small handles or protrusions from the posture training mat 80 that enable a person to center themselves on the mat along the length axis 16, or centerline axis 98, as shown in FIG. 3. Also, the posture training mat 80 may have a friction material 89 along the base surface 96 to prevent the posture training mat 80 from slipping during use, as best shown in FIGS. 5 and 6. A friction material may have a coefficient of friction of about 0.5 or more, about 0.6 or more or even 0.7 or more, according to ASTM C1028. The friction material 89 may include an elastomeric material such as urethane or silicone which provides a high friction on most flooring surfaces.

A postural awareness system 11 may utilize a mobile electronic device 21, such as a mobile phone or tablet computer to interface with the postural awareness device 10 via a mobile device wireless signal transceiver 23 and produce a feedback signal, and/or provide other feedback such as the number of pelvic tilt repetitions performed, the amount of compression of the sensor body as determined by the hall effect sensors, the alignment of compression as determined by the hall effect sensors. The postural awareness device 10 may have a wireless signal transceiver 24 that sends a wireless signal to the mobile device wireless signal transceiver 23 with information about the pelvic tilts.

As shown, the interface screen 25 is displaying 18 REPS or repetitions performed. A mobile device has an interface screen 25 that may be used to interface with the postural awareness device. The interface screen may be a light device and display a feedback light 270 or feedback symbol or text to let a user know if they have compressed the sensor body above a threshold amount and/or if the compressions are aligned during pelvic tilts. Also, a mobile electronic device may have a sound device 278 that emits a sound as a feedback sound, again to indicate actuation of the magnet to within a threshold sensor distance from the hall effect sensors and/or alignment of compression. Also, a mobile device may have a vibration device 275 that produces a feedback vibration.

Figure 2:
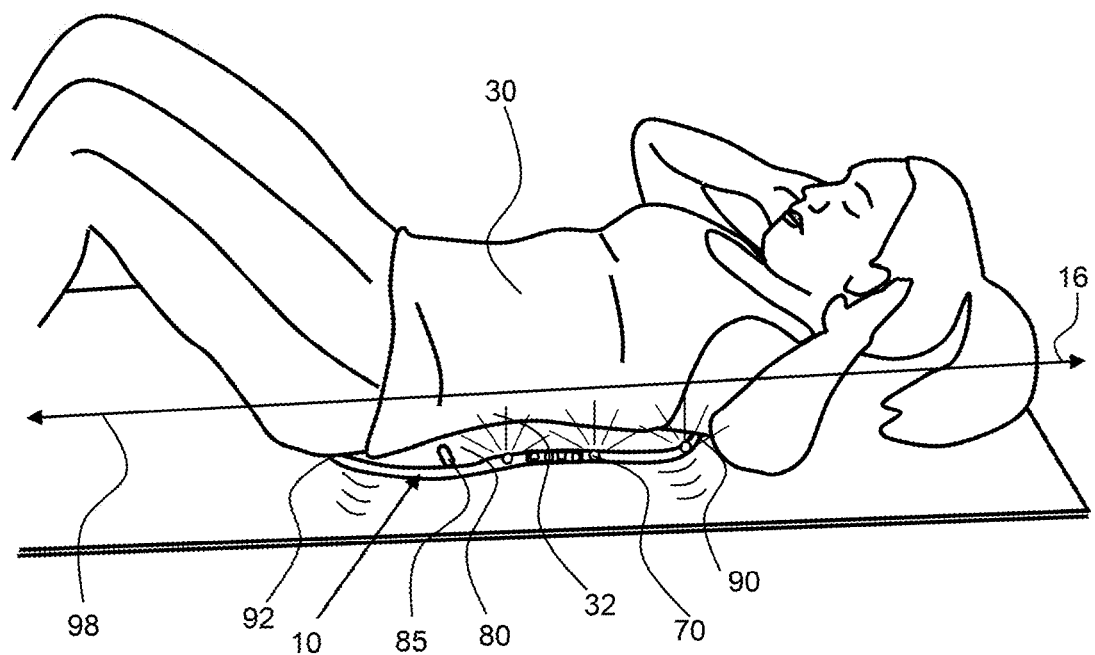
FIG. 2 shows a person exercising and pressing their lower back or lumbar down to compress the elastomeric component of the lumbar sensor and move the magnet toward the hall-effect sensor to initiate the feedback of a light and/or a vibration from a vibration sensor.

As shown in FIG. 2, a person 30 is exercising on a postural awareness device 10 and is lying on the posture training mat 80 and aligned along the length axis 16 or centerline axis 98 with their head extending from the head end 90 of the posture training mat 80 and their feet distal the feet end 92 of the posture training mat 80. When aligned with the length axis, the person's spine will extend along the centerline axis 98 of the posture training mat 80. The centerline axis extends centrally between the left and right sides of the posture training mat and along the length axis. The person may center themselves on the posture training mat 80 by grasping the alignment features 85 as shown in FIG. 3. After getting aligned, the person 30 may then press their lower back or lumbar 32 down to compress the pliable extension and move the magnet toward the hall-effect sensors to initiate one or more of the feedback devices to activate. For example, (with reference to FIG. 1) when the sensor body 42 or pliable extension 46 of the sensor body is compressed an effective amount down toward the hall effect sensors 62, a light device 70 may illuminate and/or a vibration device 75 may vibrate to produce a haptic vibration (as indicated by the curved lines around the mat), and/or a sound device 78 may emit a feedback sound.

Figure 4:
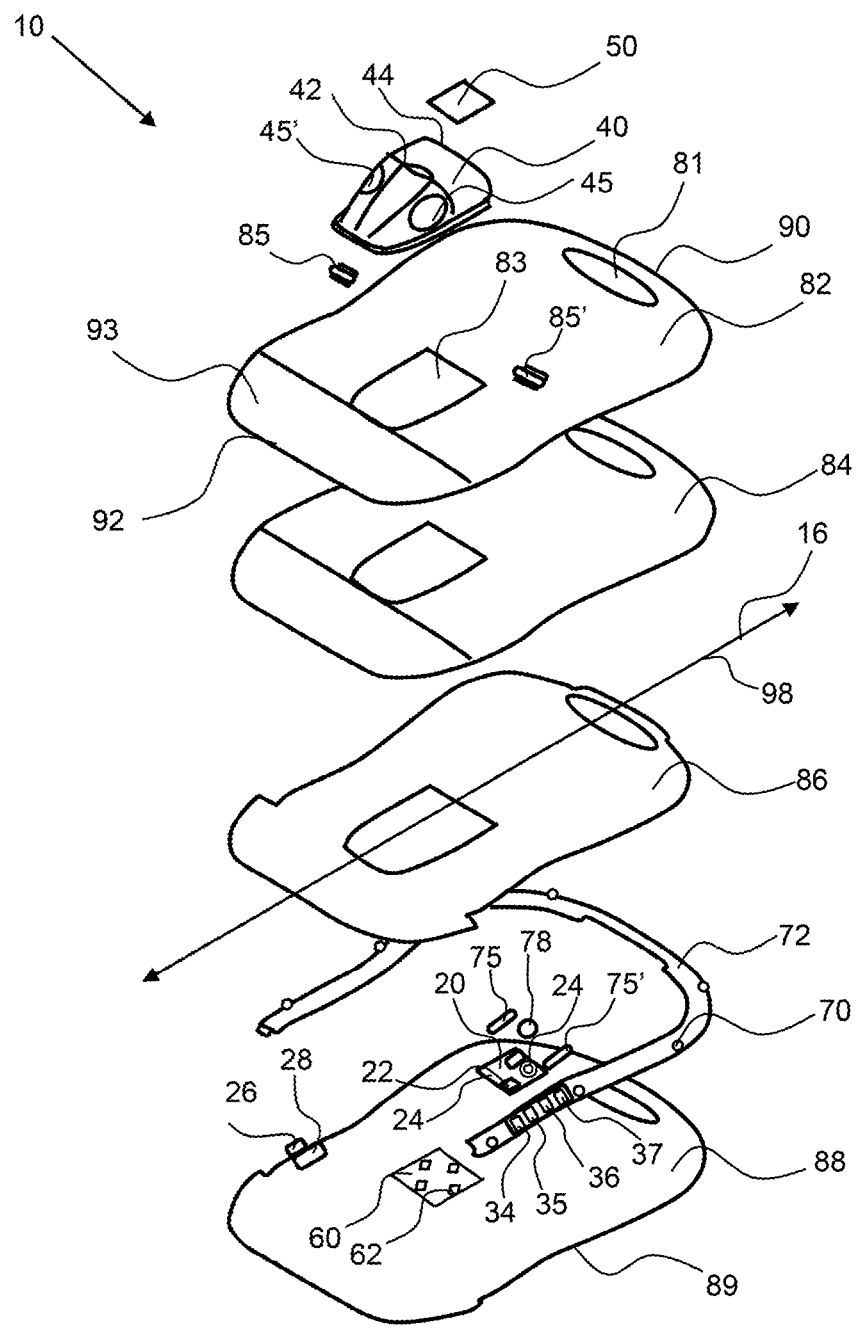
FIG. 4 shows an exploded view of the components of an exemplary postural awareness device.

As shown in FIG. 4, an exemplary postural awareness device 10 has a plurality of components that are configured to enable ease of use and effective feedback of proper lumbar positioning during an exercise. The posture training mat 80 has a base layer 88, which may have a friction material 89 configured thereon to prevent slipping or sliding of the posture training mat 80 during use, an interface layer 84 and may have a middle layer 86. Each of the layers may be a foam and may be foams of different durometer to provide the proper resistance to compression and comfort during exercise. A cover layer 82 may be configured over the interface layer to protect the interface layer from getting contaminated with sweat. The cover layer may be water resistant or waterproof and may have an attractive design and or logos printed thereon. A lumber sensor aperture 83 may be configured through the cover layer 82, the interface layer 84 and also the middle layer 86 to enable the lumbar sensor body to extend therethrough to the base layer 88. A frame component 72 may extend around a portion of the posture training mat 80, such as along or around an edge 97 of the posture training mat, and light devices 70 may be coupled to the frame and emit a feedback light from said edge of the posture training mat. A pair of vibration devices 75, 75' are coupled to the posture training mat 80 and are configured to vibrate when the magnet 50 is forced into a threshold sensor distance from the hall effect sensor 62.

The postural awareness device 10 may be controlled by a controller 20 that may have a microprocessor 22 and/or a circuit board 24 to control the functions of the device. The hall effect sensors 62 may provide an input to the controller 20 when the magnet 50 is actuated within a threshold sensor distance of the hall effect sensor 62 and the controller may then initiate the light devices 70 to illuminate and/or the vibration devices 75, 75' to vibrate, and or the sound device 78 to emit a sound. The system may have a battery 28 to power the electronic components and an on/off switch 26.

Also shown in FIG. 4 are switches for controlling the feedback devices including a sound switch 37 to turn on/off or change the sound level of a sound device, a light switch 36 to turn on/off or change the light level of a feedback light, a vibration switch 35 to turn on/off or change the vibration level (amplitude and/or frequency) of a sound vibration device. Also, a deflection switch 34 may be used to change a threshold sensor distance, the distance required to actuate the magnet toward the hall effect sensors to activate feedback devices. Some people have a greater arch in their back and therefore a lower actuation or movement of the magnet may be desirable to initiate the positive feedback.

Figure 7:
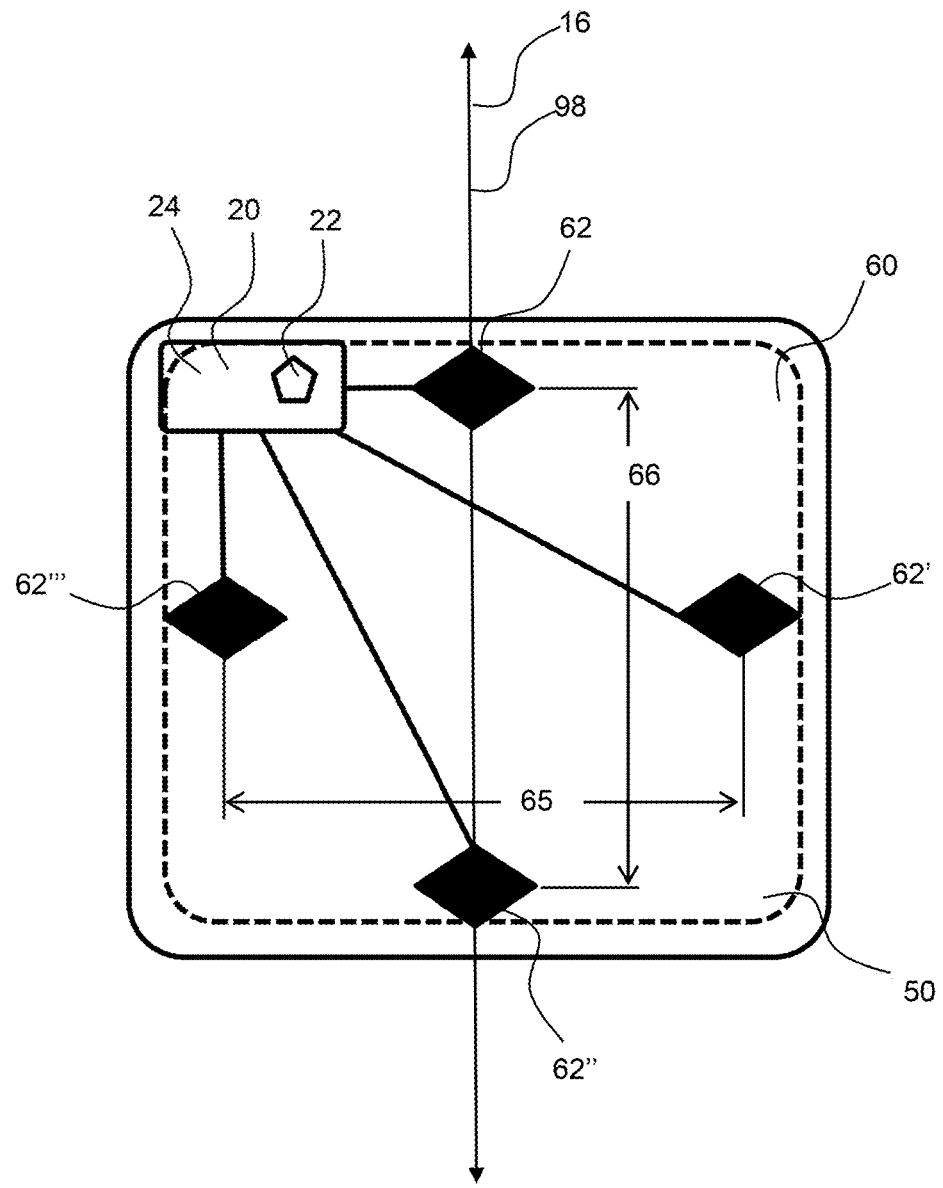
FIG. 7 shows a top view of portion of a lumbar sensor including a hall effect board having a plurality of hall effect sensors configured offset distances from each other.

Referring now to FIGS. 4 and 7, an exemplary postural awareness device 10 has a lumbar sensor 40 that is configured to detect when a magnet 50 is moved or forced within threshold sensor distance of the hall effect sensor(s) 62. A shown in FIG. 5, the magnet 50 is configured an offset magnet distance 54 from the interface surface 94 of the posture training mat 80 and a sensor distance 55 from the hall effect sensor 62. The magnet is configured on the sensor body 42, such as being coupled with the pliable extension 46 of the sensor body. The sensor body has an elastomeric component 48 that is resilient and compressible. The elastomeric component can be compressed by force from a person's lumbar, as shown in FIG. 6, and then return to an original shape upon removal of the compressing force. The sensor body may have an interior 44 requiring the sensor body to be compressed to move the magnet 50 toward the hall effect board 60 (having a plurality of hall effect sensors 62) wherein the interior surface 43 is moved toward the interface surface 94 of the posture training mat 80. The interior 44 of the sensor body 42 may be void or comprise the elastomeric component 48 that is resilient. The sensor body is compressed in FIG. 6 to move the magnet 50 toward the hall effect sensors 62 and reduce the sensor distance to a threshold sensor distance 56 to initiate the feedback devices, the light devices 70, 70' and vibration devices 75, 75' and the sound device 78.

The lumbar sensor 40 may include a plurality of hall effect sensors 62, 62', 62" 62" as shown in FIG. 7. The arrangement of the hall effect sensors, such as on a hall effect board 60 enables the controller to determine if the pelvic tilt is being performed uniformly or along the centerline axis 98 of the posture training mat 80. As shown, a plurality of hall effect sensors are configured with a length offset distance 66 along the length axis 16 or centerline axis 98 and also a width offset distance 65 orthogonal from the length axis 16, or across the width of the posture training mat. The hall effect sensors may be configured within an area spanned by the magnet, wherein the length and width of the magnet overlap the hall effect sensors, as shown. An exemplary lumbar sensor 40 may include a plurality of hall effect sensor to determine proper pelvic tilt such as two or more, three or more, four or more, five or more, six or more and any range between and including the numbers provided.

As described herein and with reference also to FIG. 1, the light devices 70 may illuminate different colors depending on the sensor distance 55 (shown in FIGS. 5 and 6) achieved by the compression of the sensor body by the lumbar. A blue light may illuminate from a light device when in a resting position. A green light may illuminate from a light device when a person is in a proper position on the posture awareness mat and has actuated the magnets threshold distance toward the hall effect sensor. A red light may indicate an improper position of the magnet or that the magnet has not been actuated uniformly toward the hall effect sensors, wherein the magnet distance from a first hall effect sensor is a threshold sensor distance differential from the distance of the magnet to a second hall effect sensor. If the sensor distance differential is above a threshold this indicates a pelvic tilt that is not in alignment along the centerline of the posture training mat, which can result in injury. As described herein a plurality of hall effect sensors may each detect a distance from the magnet and therefore a discrepancy in this measured distance from one hall effect sensor to another may initiate the red light to illuminate from a light device.

Likewise, the vibration device(s) 75 may vibrate at a particular frequency and amplitude when the magnet 50 is forced to a first threshold distance, a sensor distance 55 within a particular range or below a threshold, and then vibrate at a different frequency and/or amplitude when the magnet is forced further down toward the hall effect sensor to a smaller threshold distance, a smaller sensor distance 55. The vibration frequency may change continuously as a function of the threshold distance or may have steps in frequency for different set threshold distances.

Likewise, the sound device 78 may emit a particular sound or volume of sound, or frequency of sound, when the magnet 50 is forced to a first threshold distance, a sensor distance 55 within a particular range or below a threshold, and then emit a different sound, sound level or different frequency when the magnet is forced further down toward the hall effect sensor to a smaller threshold distance, a smaller sensor distance 55. The sound device may change the sound emitted continuously as a function of the threshold distance or may have steps in frequency for different set threshold distances. For example, the sound frequency may start of after a first threshold sensor distance is achieved and then the frequency may be increased as the sensor distance is reduced by the compression of the sensor body.

It will be apparent to those skilled in the art that various modifications, combinations, and variations can be made in the present invention without departing from the scope of the invention. Specific embodiments, features and elements described herein may be modified, and/or combined in any suitable manner. Thus, it is intended that the present invention cover the modifications, combinations and variations of this invention provided they come within the scope of the appended claims and their equivalents.

What is claimed is:

1. A postural awareness system comprising a postural awareness device comprising:
    a) a posture training mat comprising:
        i) a length from a feet end to a head end;
        ii) a width from a left side to a right side;
        iii) an interface surface;
        iv) a base surface;
    b) a lumbar sensor comprising:
        i) a sensor body;
        ii) an elastomeric component;
        iii) a magnet coupled to the sensor body and configured an offset magnet distance from the interface surface of the posture training mat;
        iv) a plurality of hall effect sensors comprising:
            a first hall effect sensor;
            a second hall effect sensor; and
            a third hall effect sensor configured a length offset distance from the first hall effect sensor;
        wherein said first hall effect sensor is configured a width offset distance of 20 mm or more from a second hall effect sensor;
        wherein each of the first hall effect sensor, the second hall effect sensor and the third hall effect sensor is coupled to the posture training mat; and
        wherein the lumbar sensor is configured to detect when the magnet is moved within a threshold sensor distance from the first hall effect sensor and the second hall effect sensor;
    c) a feedback device to produce a feedback signal, wherein the feedback device comprises a vibration device;
    d) a controller that receives input from the lumbar sensor and initiates the feedback device when the magnet is moved within said threshold sensor distance from the first hall effect sensor and the second hall effect sensor; and
    e) a battery to power the lumbar sensor and the controller and the feedback device;
        wherein the vibration device produces a feedback vibration when the magnet is moved within said threshold sensor distance from the first hall effect sensor; and
        wherein the vibration device changes the feedback vibration when the first hall effect sensor and a second hall effect sensor of the plurality of hall effect sensors detect that the magnet has been actuated a threshold sensor distance differential between the first hall effect sensor and the second hall effect sensor.

2. The postural awareness system of claim 1, wherein the plurality of hall effect sensors further comprises a fourth hall effect sensor wherein the second and fourth hall effect sensors are configured a width offset distance from each other.

3. The postural awareness system of claim 1, wherein the plurality of hall effect sensors are configured in a triangular array with said first hall effect sensor and said second hall effect sensor of the plurality of hall effect sensors configured a width offset distance from each other and said third hall effect sensor of the plurality of hall effect sensors configured a length offset distance from the first and second hall effect sensors.

4. The postural awareness system of claim 3, wherein the first and second hall effect sensors are configured across a centerline of the posture training mat and the third hall effect sensor is configured along a centerline axis a length offset distance from the first and second hall effect sensors.

5. The postural awareness system of claim 1, further comprising a light device that produces a feedback light.

6. The postural awareness system of claim 5, wherein the light device produces said feedback light when the magnet is moved within said threshold sensor distance from the first hall effect sensor.

7. The postural awareness system of claim 5, wherein the light device is configured along an edge of the posture training mat.

8. The postural awareness system of claim 7, comprising a plurality of light devices configured along said edge of the posture training mat.

9. The postural awareness system of claim 5, further comprising a sound device that produces a feedback sound.

10. The postural awareness system of claim 9, wherein the sound device produces a first feedback sound when the magnet is moved within said threshold sensor distance from the first hall effect sensor.

11. The postural awareness system of claim 10, wherein the sound device produces a second feedback sound when the magnet has been actuated a second threshold distance toward the first hall effect sensor, wherein said second threshold distance is less than said first threshold distance.

12. The postural awareness system of claim 10, wherein the sound device changes a sound frequency when the magnet has been actuated to a second threshold distance toward the first hall effect sensor, wherein said second threshold distance is less than said first threshold distance.

13. The postural awareness system of claim 10, wherein the sound device changes said feedback sound when the first and second hall effect sensors detect that the magnet has been actuated said threshold sensor distance differential between the first hall effect sensor and second hall effect sensor.

14. The postural awareness system of claim 13, wherein the feedback light changes color when the first and second hall effect sensors detect that the magnet has been actuated said threshold sensor distance differential between the first hall effect sensor and second hall effect sensor.

\* \* \* \* \*